United States Patent [19]

Grossman et al.

[11] Patent Number: 4,564,498

[45] Date of Patent: Jan. 14, 1986

[54] SYSTEM FOR THE ANALYSIS OF NUCLEAR FUEL RODS

[75] Inventors: Leonard N. Grossman, Bratenahl, Ohio; James D. Landry, Wilmington, N.C.; William Masaitis, Castle Hayne, N.C.; Robert O. Canada; Gerald W. McKenzie, both of Wilmington, N.C.

[73] Assignee: General Electric Company, San Jose, Calif.

[21] Appl. No.: 436,921

[22] Filed: Oct. 26, 1982

[51] Int. Cl.[4] .............................................. G21C 17/00
[52] U.S. Cl. ...................................... 376/245; 376/257
[58] Field of Search ................... 324/201; 376/245, 257

[56] References Cited

U.S. PATENT DOCUMENTS

| | | | |
|---|---|---|---|
| 3,787,761 | 1/1974 | Grossman et al. | 324/34 R |
| 4,134,064 | 1/1979 | Jacobs et al. | 324/201 |
| 4,243,939 | 1/1981 | Grossman et al. | 324/201 |
| 4,347,622 | 8/1982 | Bernatowicz et al. | 376/245 |

Primary Examiner—Sal Cangialosi
Attorney, Agent, or Firm—Ivor J. James, Jr.; Samuel E. Turner; Raymond G. Simkins

[57] ABSTRACT

A method and system for quality control of nuclear fuel materials, said system including amplifier/integrator circuitry, signal processors, and drift control feedback circuitry. The invention permits the qualitative and quantitative measurement of paramagnetic additives such as gadolinium for example in a paramagnetic base nuclear fuel material including ferromagnetic impurities. Drift problems relating to temperature and other effects are solved electrically and mechanically. Analysis can be conducted irrespective of the form or composition of the nuclear fuel.

9 Claims, 17 Drawing Figures

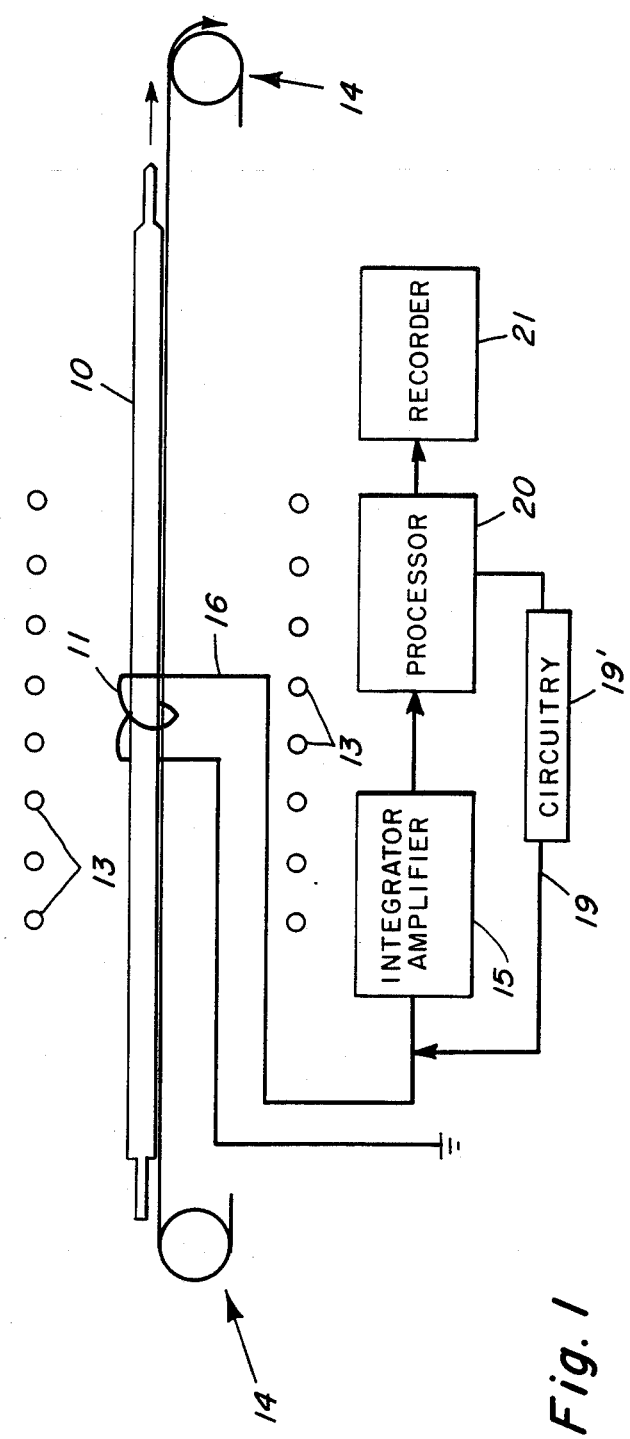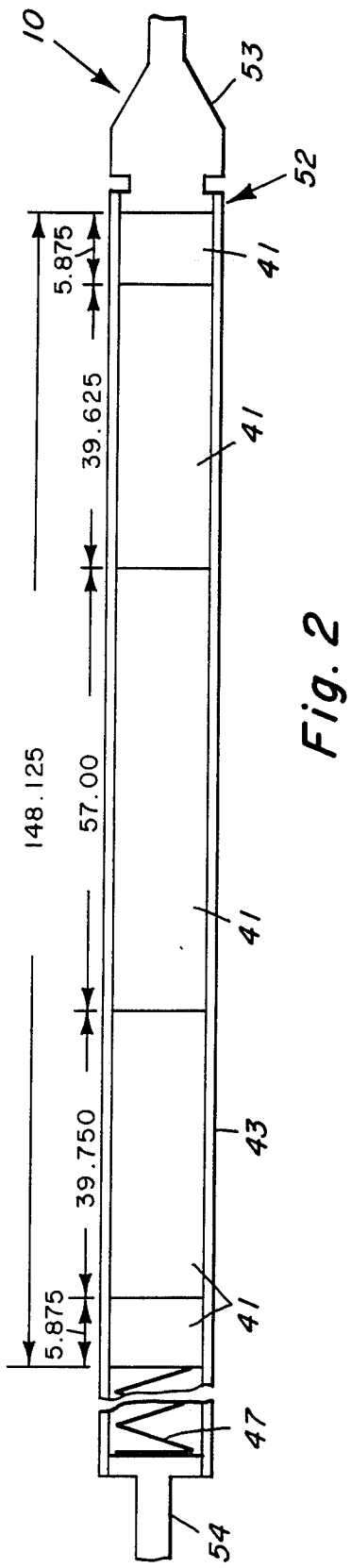
Fig. 1
Fig. 2

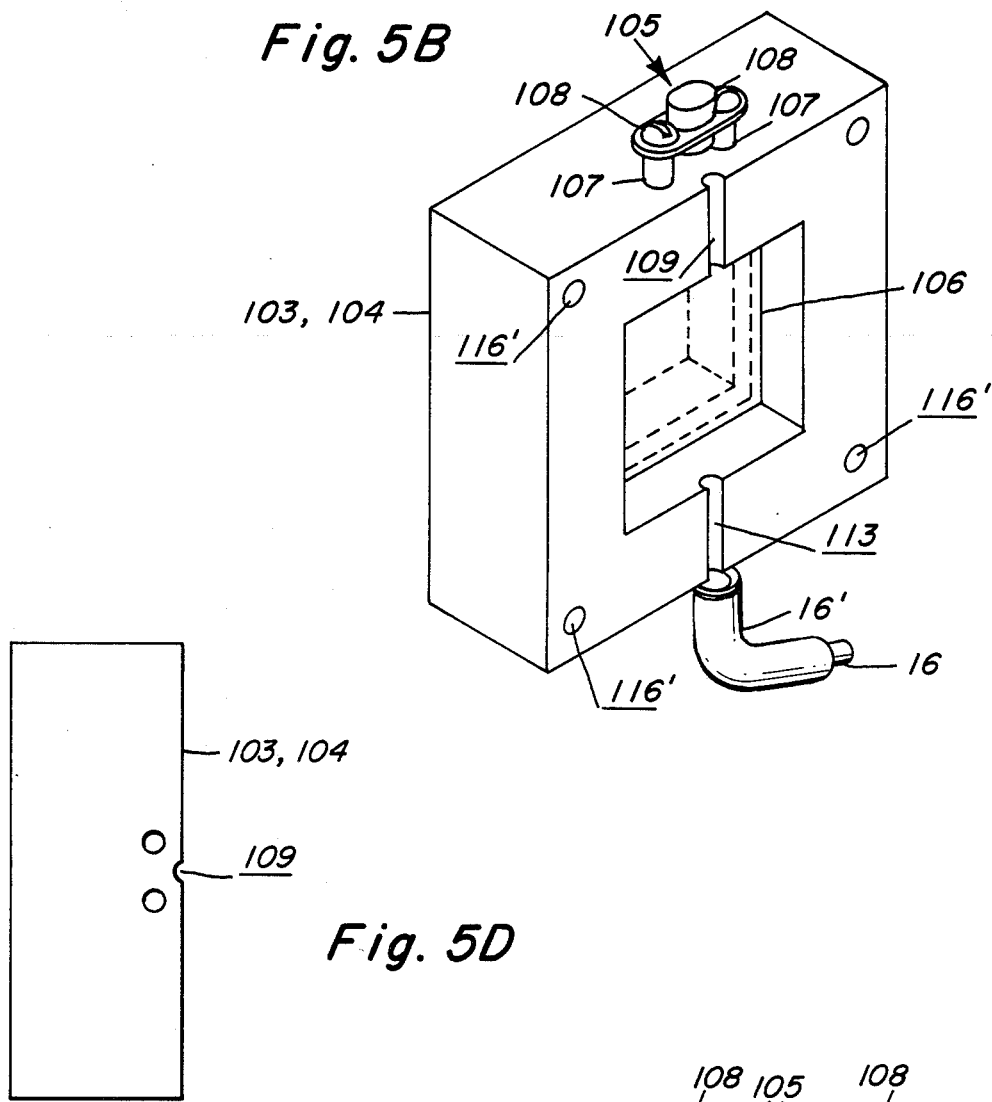
Fig. 5B
Fig. 5D
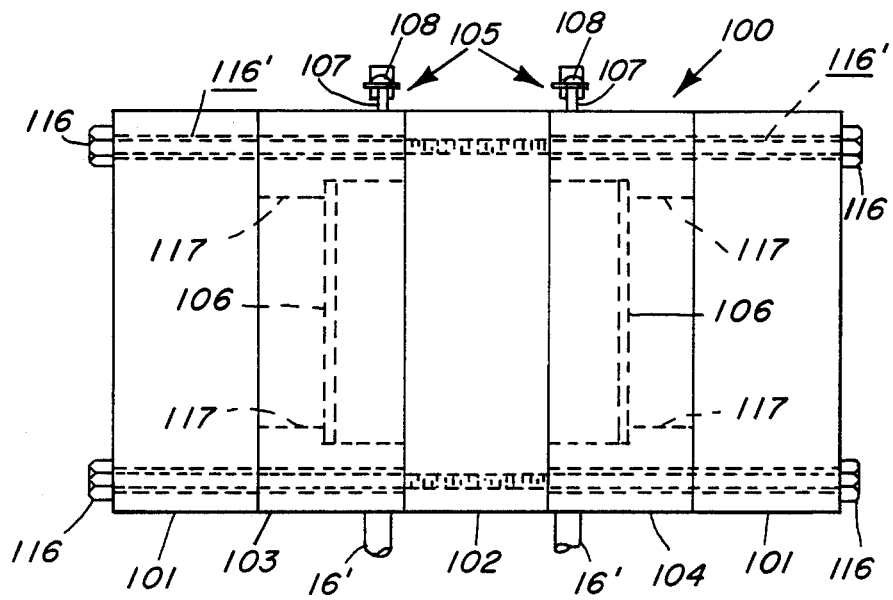
Fig. 5C

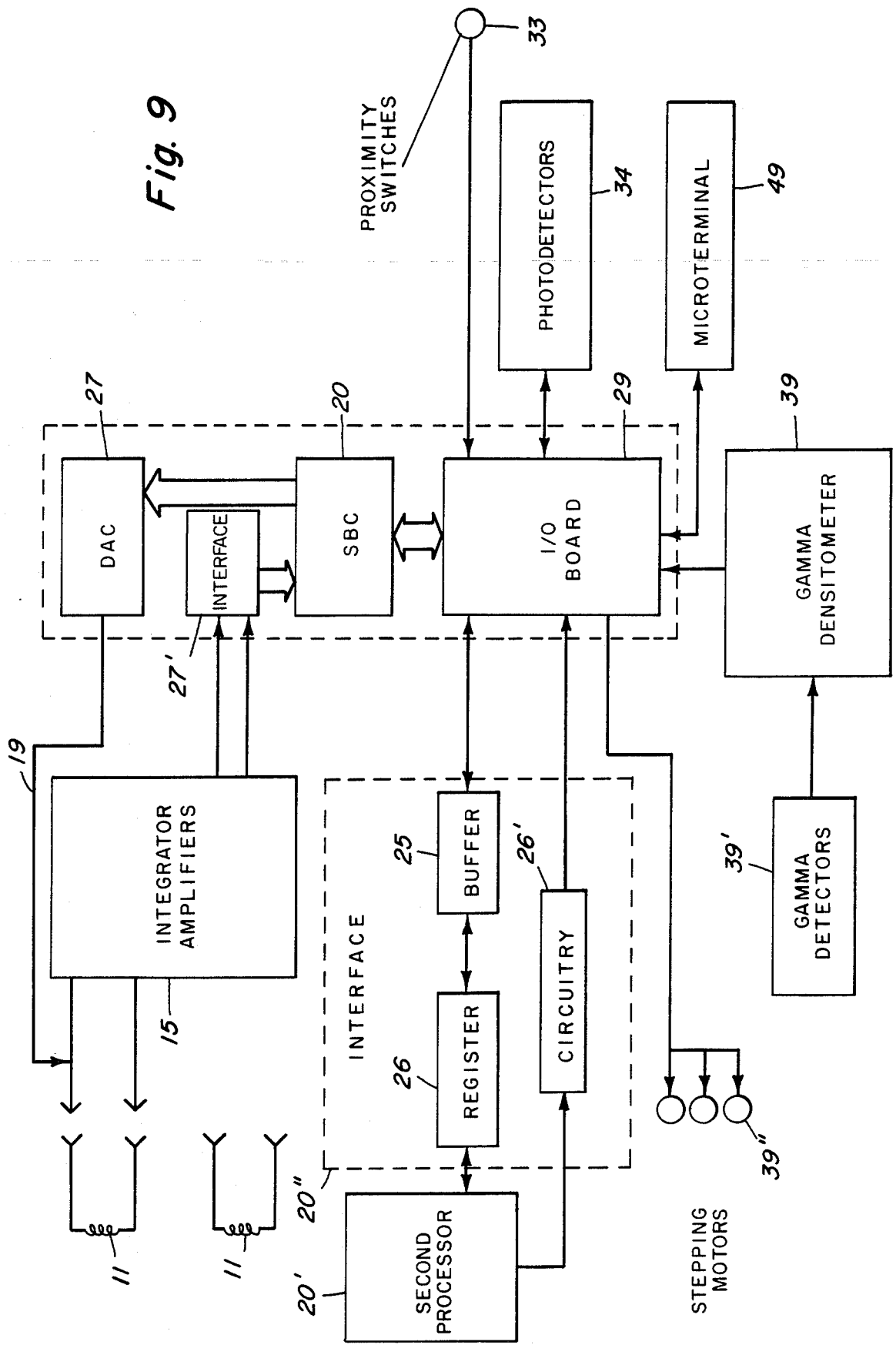

SYSTEM FOR THE ANALYSIS OF NUCLEAR FUEL RODS

BACKGROUND

This invention relates to quality control and reliability in the automated fabrication or manufacture of nuclear fuel materials. These materials can be used in nuclear reactors for power production.

Such quality control promotes the operational reliability of nuclear fuels. It is important to qualitatively and quantitatively determine the amounts and distribution of the various materials which can be combined to constitute an amount of nuclear fuel. Of particular interest is to obtain the neutron absorber profile of nuclear fuel rods to maintain quality control over neutron absorber materials.

These fuel rods are generally tube-like with the ends suitably plugged to contain, among other things, right cylindrical nuclear fuel pellets. A fuel rod may include nuclear fuel materials in suitable form such as a powder or pellets. These are enclosed within a corrosion-resistant, non-reactive cladding which is sealed on each end with an end plug, usually of the same composition as the cladding. Such fuel rods are generally described in U.S. Pat. Nos. 3,382,153; 3,349,004; and 3,741,768 (expressly incorporated herein and assigned in each case to General Electric Company). These fuel rods have been referred to by other names including "fuel elements" or "fuel pins" in the literature. Insofar as the term fuel rods is employed herein, the term is intended to apply to fuel elements and pins as well.

Fuel rods may, for example, contain about 3.3 kg of uranium dioxide pellets sealed in a zirconium alloy tube. A plurality of such fuel rods may be grouped together at fixed distances from each other in a coolant flow channel or region as a fuel assembly and typically a sufficient number of fuel assemblies is combined to form a nuclear reactor core capable of a self-sustained fission reaction, as is described in *Nuclear Power Engineering* by M. M. Eli-Wakil, published by McGraw-Hill Book Company In 1962. Further information in this regard may be found in a volume edited by D. M. Considine: *Energy Technology Handbook* (McGraw-Hill, 1977).

Furthermore, in neutron-absorber-type nuclear fuels, the neutron absorber material mixed with fissile uranium is gadolinium. The magnetic susceptibilities of uranium and of gadolinium ions are significantly different. Accordingly, it is possible to measure magnetic susceptibility as a function of length along selected fuel rods by passing them through inductive detector coils in magnetic fields at constant velocity and measuring certain response signals. This permits the accurate measurement of the distribution of additives such as gadolinium in nuclear fuel rods by magnetic measurement techniques.

Uranium is commonly used in various forms as a reactor fuel, for reasons of both availability and use. It can be employed in the form of a pure metal, as a constituent of an alloy, as an oxide, carbide, nitride, or other suitable compound.

In the embodiment herein, a ceramic fuel of enriched uranium dioxide is employed. In manufacturing production, the uranium dioxide is ground into a fine powder and compacted by cold pressing into small cylindrical pellets and then sintered in a neutral or reducing atmosphere and thereby increased in density. The pellets are ground to specific dimensions and are loaded into long, thin zircaloy tubes which serve as cladding. When the tubes are fully loaded, an expansion spring is inserted at the top, the space (plenum) is filled with helium, and finally an end cap is suitably sealed or welded in place. Inspection of the fuel pellets after grinding, of the zircaloy tubing during fabrication, and of the completed fuel rod (or fuel pin) provides assurance that all specifications are being met. Rods which pass the inspection tests are then assembled into bundles, with appropriate spacers according to reactor type.

The materials selected for nuclear fuel use according to the instant invention include fissile and fertile materials and certain neutron absorbing additives. Suitable neutron absorber materials, specifically "burnable" neutron absorber materials include, for example, gadolinium and europium. The *Naval Reactors Physics Handbook*, Vol. I, (AEC, 1964), for example, includes at pg. 817 the following list of materials potentially useful as burnable absorbers (i.e., poisons): boron, silver, cadmium, indium, samarium, europium, gadolinium, dysprosium, hafnium, lithium, erbium, iridium, and mercury. The gadolinium employed in the instant embodiment is preferably in oxide form, e.g. $Gd_2O_3$ (gadolinia). The reason for employing burnable absorbers in thermal reactors (as opposed to fast, or breeder reactors) is to compensate for the depletion of neutrons of fissile material in the fuel and an initial excess reactivity in the core in order to provide a reasonable core operation period between refueling episodes. Additionally, the nuclear fuel rods include zircaloy and steel for the construction of the tube cladding and the plenum spring respectively.

In a nuclear fuel material comprising either an elemental or compound form of uranium, plutonium, thorium or mixtures of the foregoing, various additives have been suggested to impart particular properties to the nuclear fuel material during nuclear fission chain reactions or to aid in the preparation of the nuclear fuel materials for use in nuclear reactors. Where these additives have an appropriate magnetic susceptibility or paramagnetic character, it is possible to use the magnetic response to detect the additive and to determine the amount of additive present in a nuclear fuel material, either alone or as contained in a cladding, since the nuclear fuel material and the cladding commonly used have a very low magnetic susceptibility. Representative of the additives having suitable magnetic properties which can be readily detected by the practice of the method of this invention are burnable absorber materials of gadolinium, dysprosium, europium, or erbium in elemental and compound form including respectively gadolinium oxide ($Gd_2O_3$), dysprosium oxide ($Dy_2O_3$), europium oxide ($Eu_2O_3$), or erbium oxide ($Er_2O_3$). Other additives that can be detected in elemental or compound form by the method of this invention include iron, nickel, manganese, holmium, cobalt, terbium, and thulium. Plutonium is detectable by this method when it is the only additives having any appreciable magnetic susceptibility in a nuclear fuel material.

Magnetically, $UO_2$ and $Gd_2O_3$ are paramagnetic and have susceptibilities, X, of $8.74 \times 10^{-6}$ emu/g-Oe and $147 \times 10^{-6}$ emu/g-Oe, respectively. The processing of fuel pellets for use in reactors typically introduces up to 500 ppm of elemental iron and/or ferromagnetic alloys as impurities or inclusions.

Several of the burnable absorber additives which are incorporated in nuclear fuel materials exhibit a magnetic susceptibility which is in marked constrast to the magnetic susceptibility of the other components forming the zircaloy-fuel elements including for example uranium, plutonium, and Zircaloy-2 cladding material.

It is known that the magnetic susceptibility of additives in nuclear fuel materials in comparison to the magnetic susceptibility of the nuclear fuel material and the cladding in which the nuclear fuel material is contained permits the reliable non-destructive qualitative and quantitative detection of these additives in nuclear fuel materials.

One such technique for such additive measurement is outlined in U.S. Pat. No. 4,243,939 which issued on Jan. 6, 1981 (to patentees Grossman, Portis, Bernatowicz, and Schoenig) and is assigned to General Electric Company. This patent is hereby expressly referred to an incorporated herein. Other patents of possible general interest in the subject area of magnetic detection in the nuclear arts are U.S. Pat. No. 3,787,761 (Grossman and Packard) and U.S. Pat. No. 4,134,064 (Jacobs, Lahut, and Grossman), each of them assigned to General Electric Company.

Gadolinium-bearing absorber rod designs in current use and in production since 1977 may contain zones of nominally pure $UO_2$ at both ends of the fuel rod, and zones containing $(U,Gd)O_2$ between the pure $UO_2$. These fuel rod designs are commonly called "winged" designs, and are so referred to herein. Fuel rod designs called "non-winged" designs contain no nominally pure $UO_2$ zones at either or both ends.

Assays of fuel rods can be accomplished with a satisfactory degree of precision according to the Grossman et al. technique stated in the '939 patent with respect to the winged fuel rod construction. However, the results are not equally satisfactory for non-winged designs, as shown in Table I below. The Table is stated in terms of uncertainty, which is an inverse measure of precision.

TABLE I

FUEL ROD GADOLINIA ASSAY UNCERTAINTY AT THREE TIMES VARIANCE FOR ZONE WEIGHT PERCENT GADOLINIA

| A | B | C |
| --- | --- | --- |
| Former Method For Winged Rods | Former Method For Non-Winged Rods | Present Invention For Either Case |
| ±0.18 wt. % | ±0.6 wt. % | ±0.10 wt. % |

The precision of measurements as shown in Table I are accordingly significantly better for winged rather than non-winged rods according to the former method of quality control measurement for gadolinium or other neutron absorber content. This is considered to be the result of drift problems in the electronic circuitry making the measurements, which are resolved (see Col. C) in the instant invention. The uncertainties presented in Table I are three times the variance in measurement of weight percent gadolinia per zone of fuel column. A zone length is typically about a meter, and minimum zone lengths are typically about 15 cm of fuel column. The data in Table I relating to the former method are based on the use of the nominally pure $UO_2$ wings as "internal standards"; in other words, the gadolinia content of the fuel column zones is referenced to the gadolinia-free wings. In this manner, i.e., by referencing to the wings, the measurement of susceptibility changes beyond the fuel column length is avoided. This avoidance is especially significant under the former method in view of the large susceptibility changes occurring, which are caused by the presence of ferromagnetic components such as the ferromagnetic spring in the plenum region of a fuel element. Susceptibility changes of this magnitude are hazardous to the measuring devices or circuitry employed formerly.

Drift problems may be the result of many factors including noise, interference, or thermally induced electro-motive-forces. The former measurement circuitry also has limited dynamic range with respect to input signal variations. The requirement for adequate signal resolution drives the former circuitry into saturation when large signal variations from ferromagnetic susceptibility changes occur, e.g., when the mass of a ferromagnetic spring of the plenum region of the fuel rod is passed through the measuring circuitry. The susceptibility variations ranging from air (which has a susceptibility near zero) to masses of material such as the end plugs, thermal barriers, and plenum springs within the fuel rod, are simply too great to be adequately handled with circuitry of limited dynamic range.

The drawing introduced below provides an indication of the kinds of signal variations induced in an inductive detector coil according to the Grossman technique stated in the '939 patent, when measuring a typical fuel rod. Further, a brief structural description of the fuel rod is provided.

The nuclear fuel industry has long required assurances of high quality and reliable fabrication of nuclear fuel for power production. Accomplishing this objective has caused manufacturing performance to improve in recent years and has upgraded capabilities for quality detection and control of nuclear fuel. Among other things, a computerized or microprocessor-based and controlled system for automated data acquisition and retention of fuel information has been developed.

OBJECTS OF THE INVENTION

An object of the instant invention is to make rapid, non-destructive quality control measurements of neutron absorber bearing nuclear fuel rods over the entire body of each winged or non-winged fuel rod.

Another object is to make the measuring instrumentation and equipment independent of even minor temperature and other drift producing or unstabilizing effects.

An additional object of the instant invention is to provide hybrid hardware and software for drift correction in the art of equipment effective for measuring the neutron absorber content and distribution in nuclear fuel rods.

Yet another object is to provide neutron absorber content and distribution measuring circuitry having an enhanced dynamic range.

Another object is to protect control circuitry in the nuclear fuel arts with thermal buffer means designed to minimize the temperature contribution to drift.

A further object is to provide drift correction in absorber measurement instrumentation using hybrid electrical techniques, including feedback.

Yet another object of the invention is to avoid the cumulative effects of errors that may occur when amplifier circuitry precedes integrator means in electric or electronic systems.

Still another object of the instant invention is to permit the quality control assay of the absorber content of nuclear fuel containing at least a limited amount of ferromagnetic impurities irrespective of the shape or form of said fuel material, e.g. powder, pellet, pellet-column, or fuel rod form and irrespective of variations in length, and the existence of gaps or chips in the fuel material.

SUMMARY OF THE INVENTION

These and other objects of the invention are accomplished herein by a system of electronics and software circuitry for stabilizing the measurement of the neutron absorber content in nuclear fuel rods possibly having ferromagnetic impurities. This is accomplished by a hybrid feedback network monitoring the quiescent signal output of each of two measurement circuits or channels and repeatedly feeding back low-magnitude correction signals to fine tune the circuit output. Each of the measurement circuits has an integrator stage preceding the amplifier circuitry. This avoids summing possible error quantities derived from the amplifier elements. Temperature effects are minimized by the provision of a massive metal box for packaging the electronic circuitry. Drift correction is enhanced by feedback techniques, as will be seen. The amplifier components following the initial integrator stage include a parallel portion, which insures output resolution while holding output signals within adequate scales of magnitude. This is done by connecting different gain-value amplifiers in parallel, thereby significantly increasing the dynamic range of the circuitry as a whole.

This enables the measurement of susceptibility response over the entire body of fuel rods selected for quality control measurement, irrespective of the signal magnitudes from high magnetic susceptibility portions of the fuel rod. These portions of the fuel rod include the steel plenum spring, the fuel column, and the thermal barrier effective for spreading the temperature gradient across the lowest region of the fuel rod for some designs. This measurement requires taking susceptibility measurements of air before and after each fuel rod passes through the measuring coils. Drift correction is accomplished through feedback circuitry to correct for drift variations as measured by variation in the apparent susceptibility of air.

The example of fuel plant automation of primary interest herein is a nuclear fuel rod inspection system for determining the exact uranium and gadolinium content of multizoned nuclear fuel rods. This system executes the final quality control and accountability steps in the manufacture of gadolinia containing fuel rods. It measures the exact uranium and gadolinium content of every pellet in each of these fuel rods. The system is based on a unique gadolinium detector or superconducting magnetometer in what may currently be the only known industrial use of superconductivity. The fuel rods are passed through the coils of the magnet which supply a field of 70,000 gauss. The superconducting coils of the magnet are immersed in liquid helium at 4° Kelvin. The system, is fully automated, from material handling to data accumulation, data reduction, reporting, and material accept/reject sorting. The magnet sensor provides final fuel rod inspection for pellet density variations, gaps between pellets, presence of the getter and spring, and cladding wall thickness. Under computer control, the rods pass through the magnetic station and then the passive scanning station where they are scanned for the enrichment level of every pellet, as well as for the total uranium and U-235 content in each rod.

DESCRIPTION OF THE DRAWINGS

The invention herein can best be explained in terms of a best mode or embodiment, which is set forth in detail below and shown in the illustration of a drawing of several figures, wherein:

FIG. 1 illustrates a fuel rod passing through an inductive pick-up coil located in a magnetic field.

FIG. 2 is an illustrative longitudinal cross-sectional view of a typical nuclear fuel rod.

FIGS. 5A–5D illustrate a thermal buffer which dampens the effect of ambient temperature fluctuations upon the integrator/amplifier channels protected at independent locations within the buffer.

FIG. 9 provides an overview of the system of the instant invention as applied to a single channel.

DESCRIPTION OF A PREFERRED EMBODIMENT

Figure 3A:
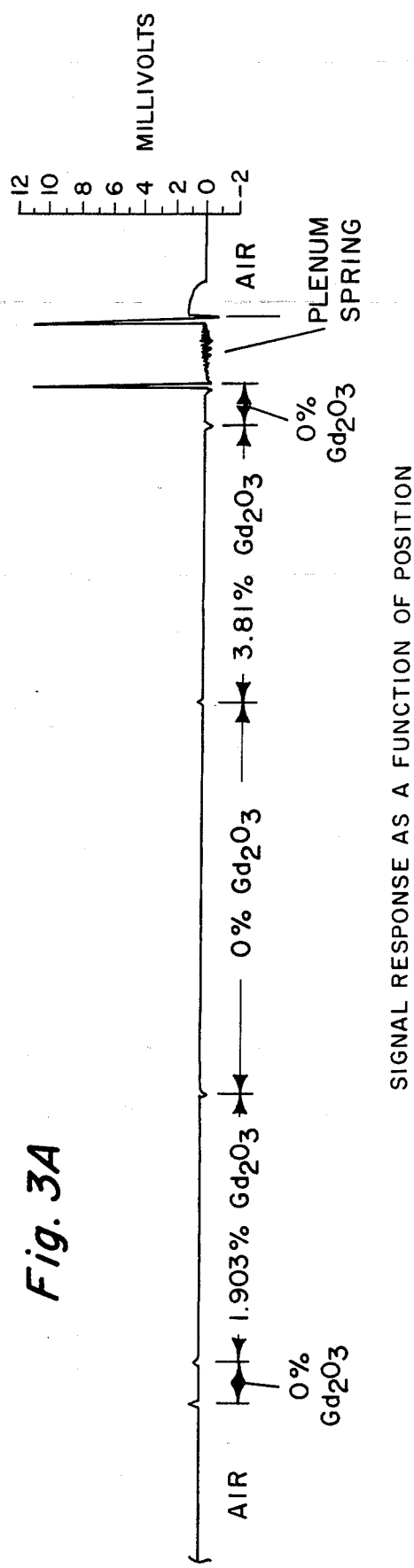
FIGS. 3A and 3B show the integrated and non-integrated signal response detected by the pick-up coil.

FIG. 1 shows a first embodiment of the instant invention, which provides for drift compensation or correction in circuitry designed for the measurement of the neutron absorber profile of a nuclear fuel rod.

More particularly, there is shown in FIG. 1 a nuclear fuel rod, pin, or element 10 including nuclear fuel material passing through an inductive means or pick-up coil 11 for detecting magnetic disturbances which is positioned in a magnetic field-producing superconducting solenoid or magnet 13, in turn held in a Dewar container (not shown) for cooling. The fuel element 10 moves at a constant velocity on a belt or other transport means 14. The coil 11 produces an electrical output indication proportional to the change in magnetic susceptibility along the fuel element as it moves through the coil 11. The electrical output indication is integrated and amplified by a system of integrator/amplifier circuitry or channels 15 and is presented to a processor 20. The output signals from the integrator/amplifier circuitry 15 are proportional to the magnetic susceptibility of the portion of the fuel material or other material, e.g., air, momentarily at the pick-up coil 11. These signals are interpreted by the processor 20 which compares them with the signals previously recorded with respect to the signal scheme derived from measuring a standard fuel element. The processed results are then made available to an information receiver or recorder 21, which may be a machine-human interface (such as a printing machine or recorder) or a link to an automated information system. A feedback signal is provided along cable 19 which connects electrically with various elements of feedback circuitry 19' to be discussed below. The coil 11 and the superconducting magnet 13 are similar to those described in the Grossman et al. '939 patent. The processor 20 can be any of or a combination of commercially available computation means such as, for example, a Digital Equipment Company Model PDP-11/34 computer system with appropriate accessories. The recorder 21 can be any of a number of devices such as a Gould Model printer/plotter.

The instant invention can analyze susceptibility changes relating to the passage of a fuel element 10 through the normally empty or "air bore" interior of the magnet 13. This permits calibration with regard to an "air-core" having no fuel rod 10 present within the detection coils 11. Formerly, such calibration was not possible because of dynamic range limitations. Calibration formerly required the presence of nominally pure $UO_2$ pellets (or a magnetically equivalent material) within the body of the fuel rod. These were typically placed at the beginning and end of a fuel column of right cylindrical pellets 41 (FIG. 2) arranged end-to-end within the cladding 43 of a fuel rod. FIG. 2 does not show individual pellets, but instead depicts zones of pellets, each zone comprising a stack of pellets having a common axis coincident with the axis of the fuel rod 10 as a whole. The spring 47 as shown in FIG. 2 is among the components of the fuel element 10.

The ends of the fuel rod are typically sealed or plugged with end plugs 53 and 54 of zircaloy material as by welding. A similar or the same alloy is suitably used for the tubing material or cladding 43 effective for holding the fuel pellets 41 in position between the end plugs 53 and 54. The several patents referred to above provide additional information as to the structure of fuel rods generally.

Figure 3B:
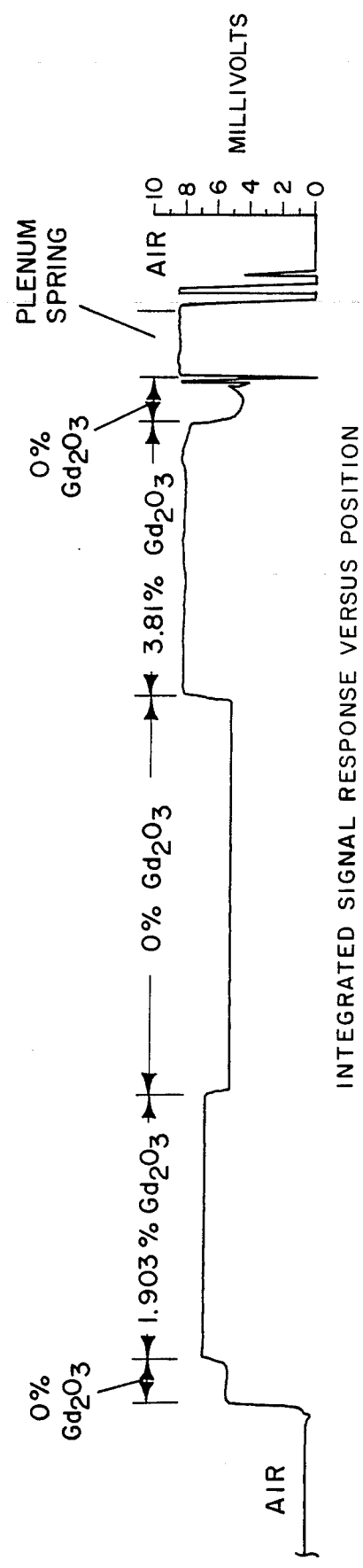

FIGS. 3A and 3B show the signal profiles f(x) and the integral $\int f(x)dx$ corresponding to a fuel rod 10 of typical construction as shown in FIG. 2 and specified in Table II below. The profile is shown in two parts: first, in terms of the direct voltages measured at the coil; and second, in terms of the integrated and amplified voltages $\int f(x)dx$ that reach the processor 20 after amplification and integration. Particularly interesting are the signal peaks at the beginning and end of a fuel rod 10, because of their magnitude, which establishes the dynamic range requirements that need to be met in the measuring circuitry. The overall profile also illustrates the effects of signal drift which can drive circuit elements into saturation. The data has been obtained for a test rod such as the one shown in FIG. 2 which has been scanned for development purposes. FIG. 3A shows the output in millivolts of a 1,000 turn copper wire pick-up coil in series with a precision adjustable resistor. The combined resistance of the coil and adjustable resistors is 15KΩ. FIG. 3B is the same signal as recorded in FIG. 3A, except that it is integrated through a prototypical integration means essentially identical to that disclosed herein. When the rod shown in FIG. 2 is scanned, electrical signals are generated in the pick-up coil which can be exhibited as shown in FIG. 3A. When those signals are integrated according to the instant invention, the integrated signal from the pick-up coil can be obtained as shown in FIG. 3B. The data of Table II below contains all necessary and sufficient information to determine the gadolinium content of a fuel rod and contains some additional information. That high quality integrated data is suitable for being digitized and transmitted to a processor for interpretation by machine intelligence in the manner disclosed herein.

Referring more particularly to FIG. 2, within the cladding 43 there is found a winged fuel column typical of current power reactor design. The column contains sintered oxide fuel pellets preferably of right cylindrical form, having a composition $(U,Gd)\text{-}O_2$. It contains two gadolinium-bearing fuel column zones, and two nominally pure $UO_2$ zones, which are the two "wings". The plenum spring 47 holds the fuel pellets 41 in place against one another. The region of the plenum spring 47 is long enough to hold fission gases which are generated during operation. Certain getter materials (not shown) may also be found within the region defined by the plenum spring 47. The interior of the cladding 43 may also include a thermal barrier (also not shown) for spreading the temperature gradient at the bottom of the fuel rod 10 across a relatively broad region at the bottom end of the cladding 43. This protects the weld joint 52 between the lower end plug 53 and the cladding 43. The fuel pellets 41 in the fuel column are generally made of enriched uranium dioxide; a neutron absorber is mixed with some of the uranium dioxide material. This fuel design involves having the concentration of absorber material vary in zones along the length of the fuel column as shown in FIGS. 3A and 3B. In particular, the absorber concentration can be modified stepwise from the bottom of the fuel column to the upper end of the fuel column. In some cases and as shown, the first and the last of the pellets 41 in the column are nominally pure uranium dioxide. This particular arrangement shown is considered to be the winged design referred to above. When the fuel column fails to have such nominally pure uranium dioxide at one end or both ends of the fuel column, the fuel design is termed non-winged. The fuel rod illustrated in FIG. 2 has no getter nor thermal barrier. The properties of the five fuel column zones (from bottom to top of fuel rod) are given in Table II.

TABLE II

| PROPERTIES OF FUEL COLUMN ZONES IN 5-ZONE FUEL ROD OF FIG. 2 | | | | | |
|---|---|---|---|---|---|
| | A | B | C | D | E |
| Wt. % $Gd_2O_3$ | 0.0 | 1.90 | 0.0 | 3.81 | 0.0 |
| Fuel Weight (gm) | 133 | 861 | 1282 | 866 | 133 |
| Zone Length (inch) | 5.88 | 39.63 | 57.00 | 39.75 | 5.88 |
| Fuel Density (% of theoretical density) | 96.22 | n.d.* | 96.22 | n.d.* | 96.22 |

*(n.d. = not determined; about 96% theoretical.)

As the Table II shows, the specific fuel rod 10 employed to produce the data in FIGS. 3A and 3B includes a fuel column which is approximately 148 inches long.

The fuel column is of the winged design and includes nominally pure uranium dioxide zones on each end of the fuel column. Each of the pure uranium dioxide zones in this instance is about 5.88 inches wide. Between the two nominally pure uranium dioxide zones, there are zones of varying gadolinium concentration. A first zone which is approximately 39.63 inches wide contains approximately 1.90 weight percent gadolinia. The last zone is approximately 39.75 inches wide and has 3.81 weight percent gadolinia. The middle zone is of nominally pure uranium dioxide and is approximately 57.00 inches wide. The uranium itself is enriched to a degree suitable for use in a boiling water reactor.

FIG. 3A shows signal peaks at certain points that correspond to the physical structure of the fuel rod 10 passing through coil 11. For example, in FIG. 3A there is a first peak which corresponds to the arrival of the fuel rod 10 at the coil 11. The corresponding signal rise is shown in FIG. 3B. This reflects the change in susceptibility of the material that has just arrived at coil 11. Clearly, the susceptibility of the fuel rod 10 within the coil 11 is significantly higher than the susceptibility of air, which is measured when the coil 11 is empty.

A next peak in FIG. 3A, smaller than the first peak, which indicates the entry or arrival of a fuel rod 10 in the coil 11, reflects a change in gadolinia concentration from zero weight percent to 1.90 weight percent gadolinia. This confirms the fact that the susceptibility of nuclear fuel including gadolinium is higher than without a gadolinium concentration in the fuel. A generally level response is shown in regions of constant gadolinium concentration, and there is no significant increase in susceptibility while zero weight percent $Gd_2O_3$ material passes through the coil 11. An inverted peak is shown in FIG. 3A representing a concentration drop of about 1.90 weight percent $Gd_2O_3$ to zero weight percent $Gd_2O_3$. This is reflected in a reduced level in the integrated response shown in FIG. 3B. The response is generally level in both FIGS. 3A and 3B until arrival of approximately 3.81 weight percent $Gd_2O_3$ concentration material in the coil 11. At that point, there is a rather significant rise in the integrated response shown in FIG. 3B.

A negative spike indicates a return to zero weight percent $Gd_2O_3$. Following thereafter there is a region of great variation corresponding to the presence of the plenum spring 47 in coil 11. After the fuel rod 10 departs from the coil 11, the response essentially returns to zero.

The base paramagnetic nuclear fuel material may include a uranium-bearing material, and the paramagnetic additive material may for example include a gadolinium material. The fuel material may be composed or selected from a group consisting for example of compounds of elements such as uranium, plutonium, thorium, gadolinium, europium, or zirconium. These compounds may be found in the nuclear fuel either singly or in plural or they may be found in mixtures or solid solutions. The fuel material may be made of an oxide compound or a carbide compound or of a nitride compound or for that matter of any related elemental compound. The fuel material itself may be in the form of a powder or in the form of pellets. It may be enclosed in cladding. The fuel may include a fissile host material and non-fissile additives. In that case, the fissile element may be uranium; and the additive, gadolinium. The additive material may be comprised of any compound exhibiting significant paramagnetic susceptibility. Fissile or additive elements may be employed and these may be oxide compounds.

Figure 4:
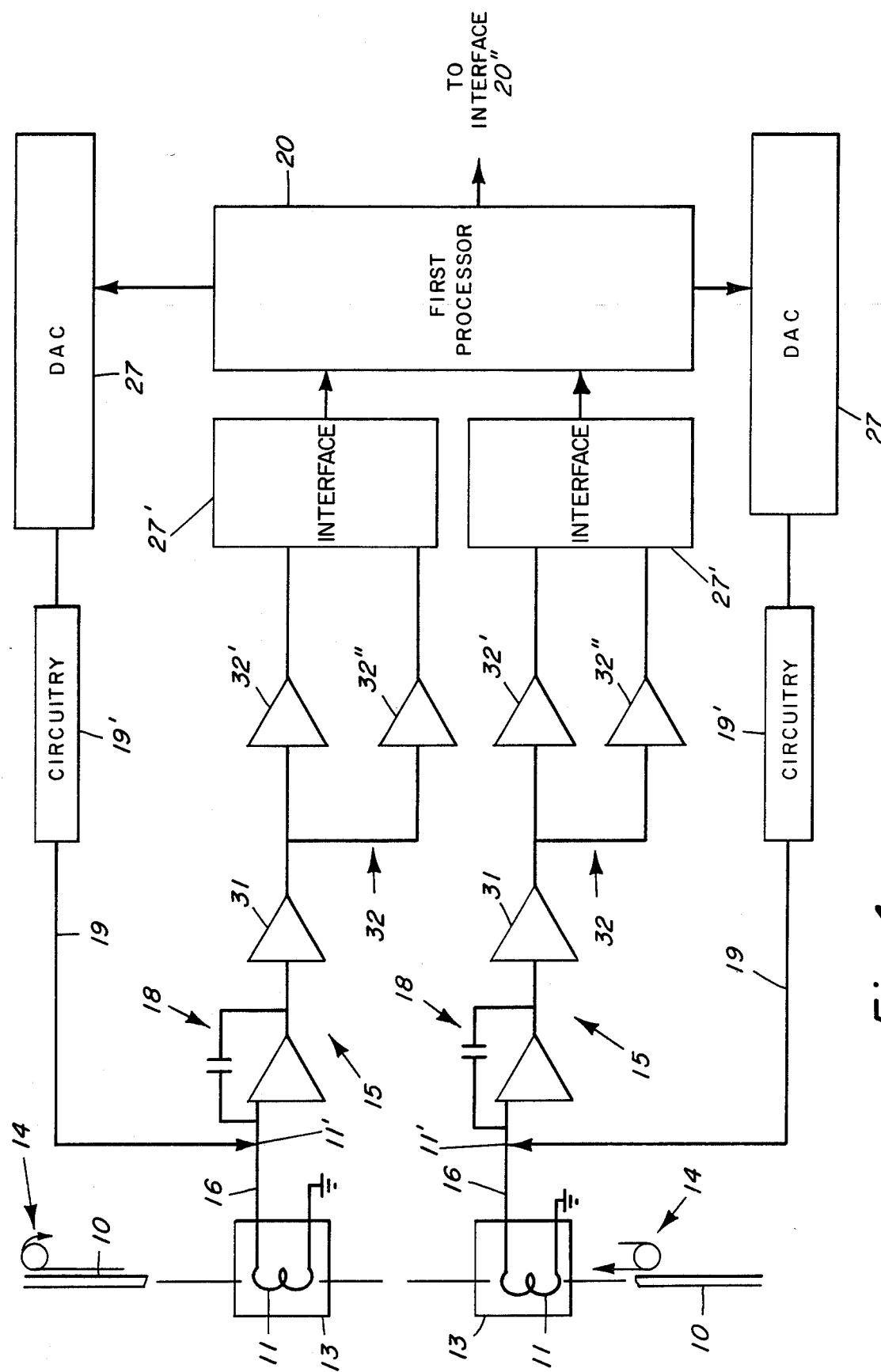
FIG. 4 depicts circuitry for integrating and amplifying signals from a pair of pick-up coils operating in magnetic fields of different strengths.

FIG. 4 shows a preferred embodiment of the invention including two pick-up coils 11, and a pair of integrator/amplifier circuits or channels 15. Nuclear fuel rods 10 are shown suitably supported and transported at a constant velocity through the two coils 11 within a single or several magnets 13. If a single magnet 13 is employed, it must be able to produce regions of significantly different bore magnetic field levels. Fuel rods 10 are shown before and after passage through two detecting pick-up coils 11 positioned coaxially adjacent one another. The system in FIG. 4 can analyze material with or without ferromagnetic impurities, as set forth in U.S. Pat. No. 4,243,939. The single-coil system of FIG. 1, on the other hand, is workable for fuel materials without ferromagnetic impurities only. Each detecting coil 11 in FIG. 4 is suitably positioned in a relatively high, constant or direct current magnetic field established in the hollow bore of respective magnets 13.

Each coil 11 is grounded and an electric lead 16 from each coil 11 connects with the integrator/amplifier circuitry 15. The ingegrator/amplifiers 15 are connected to processor 20 by way of interfaces 27'. Feedback circuits connect processor 20 with the input terminals 11' of integrator/amplifiers 15. Each feedback circuit includes a digital-to-analog converter (DAC) 27, circuitry 19' and lead 19. Each integrator element or integrator 18 is followed by a first and second amplifier stage, respectively 31 and 32. The second stage 32 in each case includes at least two amplifiers 32' and 32" in parallel to increase the dynamic range of the integrator/amplifier 15.

Figure 8A:
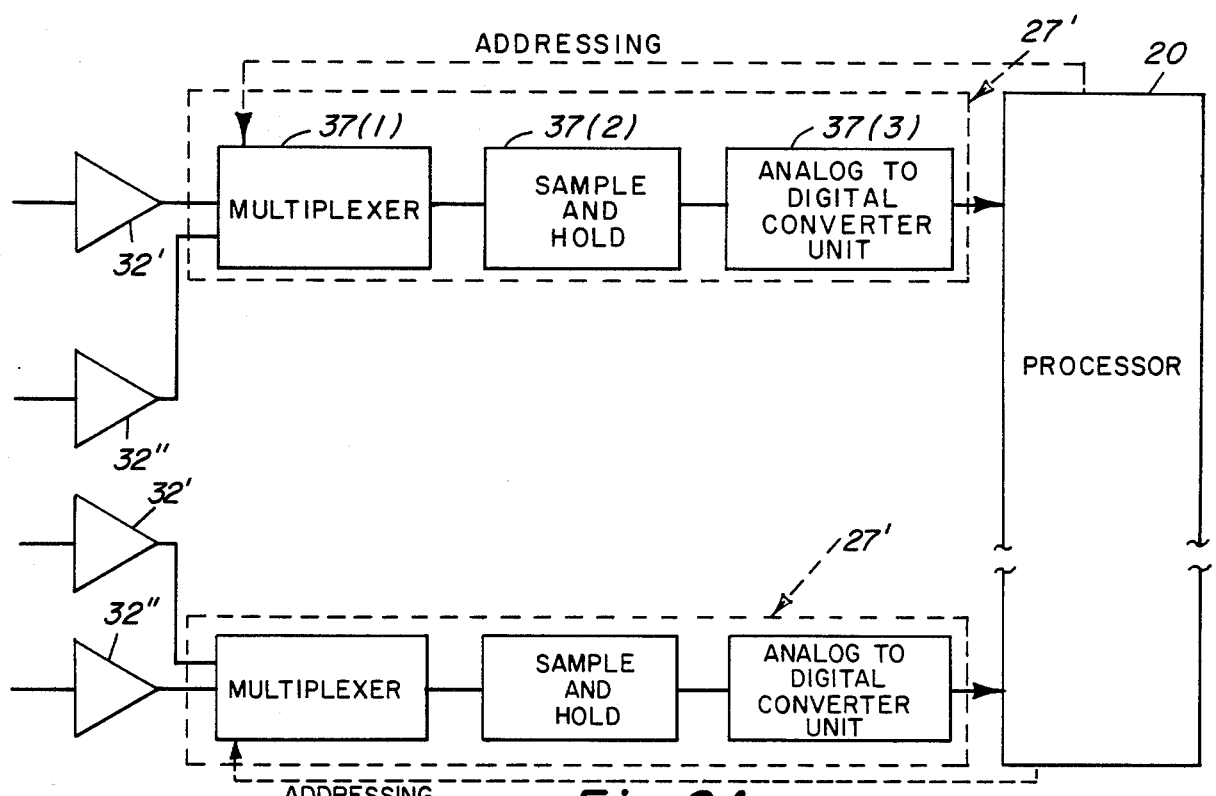
FIG. 8A illustrates the interfaces shown in FIG. 4 between the preceding integrator/amplifier circuitry and the subsequent processor.

The processor 20 repeatedly samples the output electrical signals $V_N$ of one or the other of two amplifier channels of the second amplifier stage 32 by addressing a multiplexer 37(1) as shown in FIG. 8A. Sampling may, for example, be conducted at a rate of 800 times per second. To generate a feedback signal for drift compensation, an average or mean $\overline{V_N}$ is taken of the most recent 256 samples of the high sensitivity signal, unless the high sensitivity channel is outside of the range of the analog-to-digital converter (ADC) 37(3), as will be discussed. This mean or average value $\overline{V_N}$ is compared to a recently established reference value $V_R$ to produce a feedback or drift compensation or voltage $V_C$ which is fed back to the input side of integrator 18 via the DAC 27 and attenuator circuitry 19'. Drift compensation calculation is normally performed once per minute. No drift compensation calculation is performed when a fuel rod is being scanned or during sampling. At the beginning or operation, the electrical output signal of the integrator/amplifier 15 is set at a reference level of minus five volts and is permitted to vary during operation between negative 8.75 volts and negative 1.25 volts without any attempt to conduct drift compensation. However, when the average value $\overline{V_N}$ drifts outside of this range, the processor 20 will act to readjust the output electrical signal $V_N$ to minus five volts.

Which of the parallel amplifiers 32' or 32" is used depends upon whether ADC 37(3) is saturated. Saturation is taken to occur when the output level from the high sensitivity output amplifier 32' causes ADC 37(3) to reach a level over 2,048 steps.

Figure 10A:
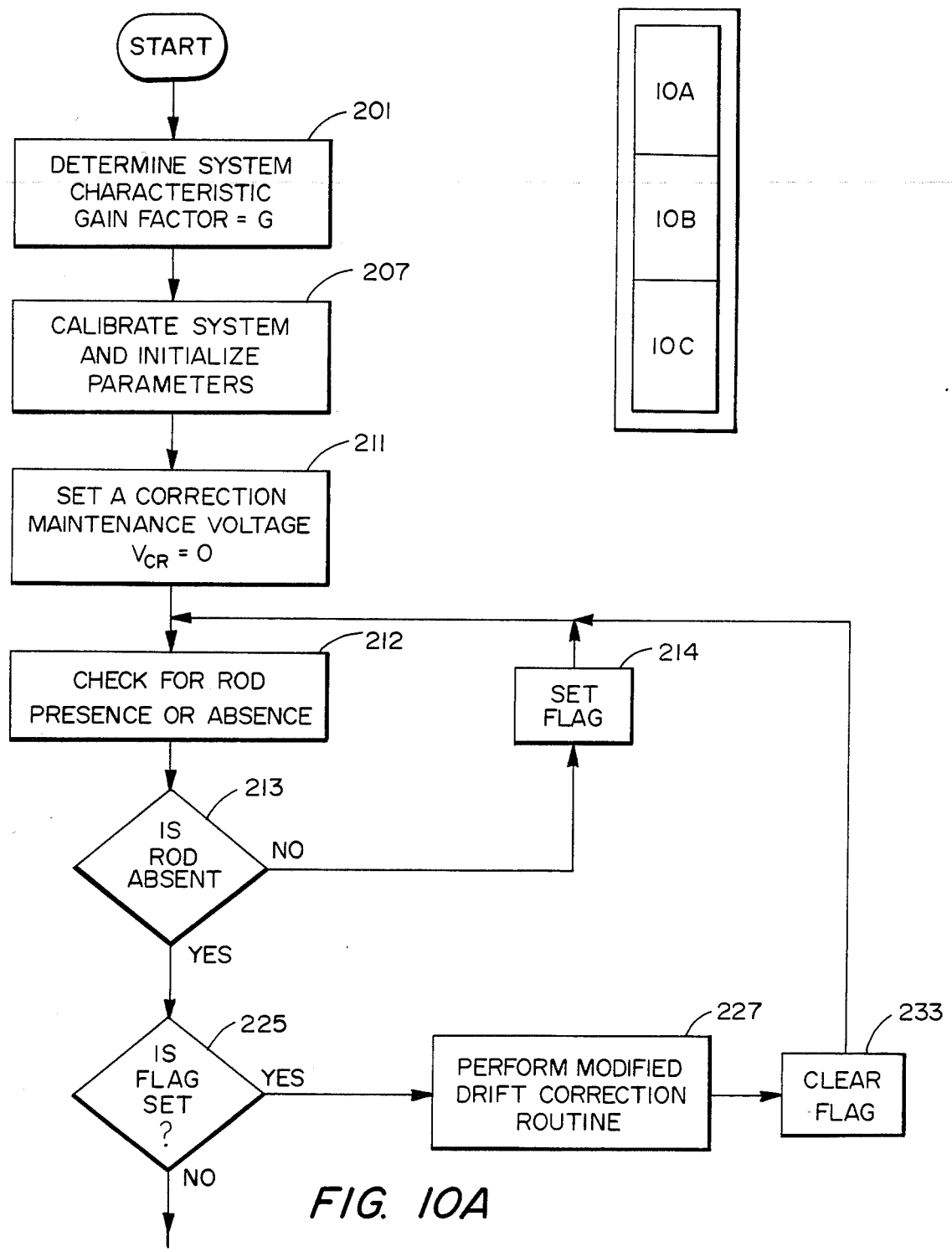
FIGS. 10A–10C show a flow chart describing the development of the drift correction signal by digital means in view of electrical indications sampled on the output side of each integrator/amplifier channel.
Figure 10B:
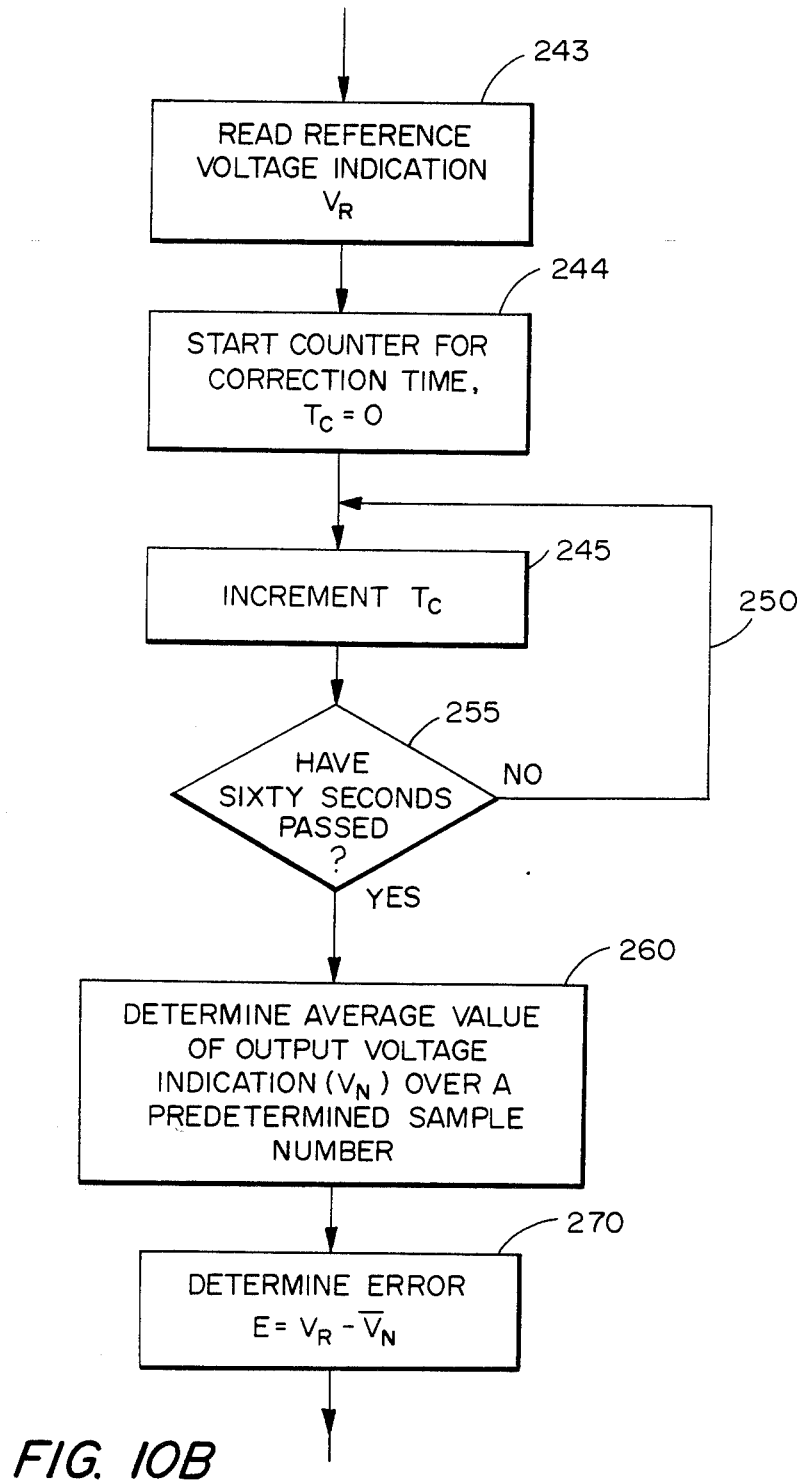
Figure 10C:
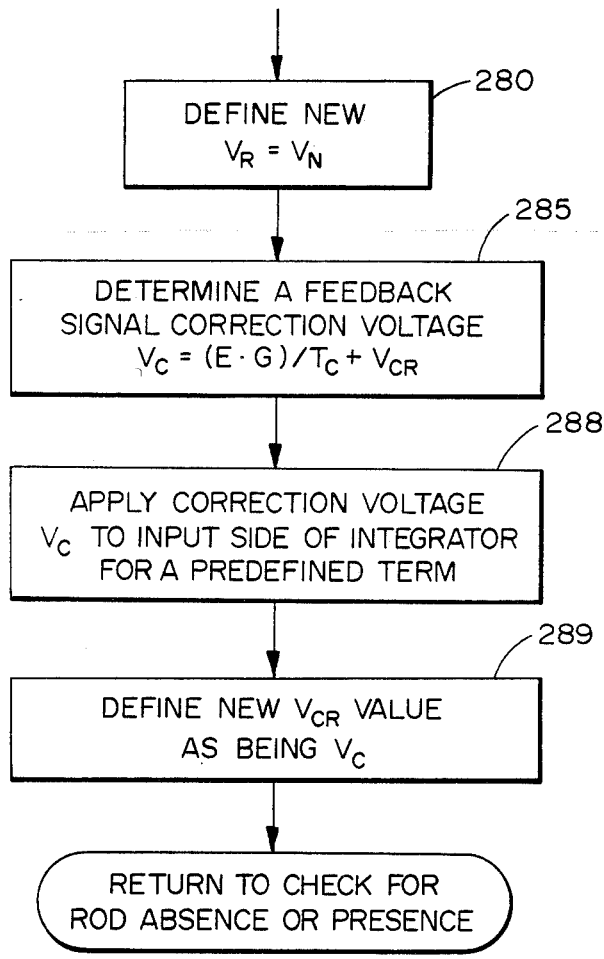

To elaborate further, FIGS. 10A–10C show a flow chart according to which the processor 20 determines the amount of drift compensation. A gain factor "G" characteristic of the integrator/amplifier circuitry 15 is initially determined as indicated at block 201 to insure that the drift compensation signal will not be too large nor too small to affect adversely system stability and operation. As will be seen below, the gain factor G assists in determining a suitable drift compensation signal $V_C$.

Additionally, internal calibration and initialization of certain parameters well known to those of ordinary skill in the art must be conducted, as indicated by block 207. This includes defining a correction maintenance voltage $V_{CR}$ equal to zero, as suggested by block 211. The value of this voltage $V_{CR}$ will insure that a drift compensation signal $V_C$ of zero or more will be provided after initial startup even when there is no difference between $\overline{V_N}$ and the most recently established $V_R$. $V_{CR}$ is permitted to float between bounds established by the dynamic range of the ADCs 37(3).

Next, the circuitry checks for the absence or presence of a fuel rod 10 as indicated as blocks 212 and 213. If a rod 10 is present, a flag is set as indicated at block 214, and operation enters a continuing loop until the rod 10 has finally been removed from the coils 11. Then a flag set check occurs, as suggested at block 225. If the flag is found to be set, thereby indicating that a rod 10 has been present, a special or modified drift compensation or correction routine is required, as indicated at block 227. This routine might be based for example on a time correction counter value $T_C$ greater than the 60 seconds. Once this has been accomplished, the flag is cleared as indicated at block 233 and a return is made to the beginning of the rod presence check block 212.

Assuming that no rod 10 is present, the return will pass through to the flag-set query at block 225 with a negative result and an output voltage $V_R$ will be read as per block 243 in FIG. 10B. The time correction counter is then initialized with its value $T_C$ set to zero, i.e., $T_C = 0$ as indicated by block 244. The counter is incremented as per block 245 by passage through loop 250 until sixty seconds have elapsed as per block 255. The fixed $T_C$ value (in this case 60 seconds) must be short in comparison with the thermal time constant of a thermal block 100, but long in comparison with the period of noise excursion in order to insure an accurate determination of drift.

At that time, an average value of output voltage $\overline{V_N}$ is determined over a predetermined sample number, as per block 260. A suitable sample number might be 256 samples as indicated above. As already noted, the value of $V_N$ is derived from either the high field or low field output, respectively 32' and 32", of the circuitry shown herein.

As suggested in block 270, an error value "E" is determined in view of the average output voltage $\overline{V_N}$ by subtracting $\overline{V_N}$ from $V_R$, the reference voltage established about sixty seconds before. Accordingly, E is a measure of the voltage drift from $V_R$ to $\overline{V_N}$ over the period of sixty seconds.

To set up a next determination of error E, the value $V_R$ is redefined as being equal to $V_N$, i.e., $V_R = \overline{V_N}$, as shown at block 280.

The magnitude of the drift correction signal or voltage $V_C$ corresponds to the error E as modified by multiplication with gain factor G divided by $T_C$, i.e., $G/T_C$, and the addition of correction maintenance voltage $V_{CR}$, as shown at block 285. In toto, $V_C = (E \cdot G)/T_C + V_{CR}$. Drift compensation voltage $V_C$ is fed back to the input of integrator 18 via DAC 27 and attenuator circuitry 19' as shown at block 288. Then a new correction maintenance voltge is $V_{CR}$ set equal to the drift compensation signal $V_C$ as shown at block 289.

The processor 20 controls the determination of the drift compensation signal. Additionally, the processor 20 transfers data from the integrator/amplifier circuitry 15 to another processor 20' shown in FIGS. 7 and 9. This processor 20' has a significantly larger data handling capacity. In particular, processor 20' employs a 16-bit wide data bus, whereas the processor 20 employs only an 8-bit wide data bus. Accordingly, an interface 20" is required to make the two processors 20, 20' compatible with one another. This is done by providing a data buffer 25 and a register 26 between the two processors 20 and 20'. The data buffer employed is 16-bits wide and 64 words deep and constitutes a first-in, first-out (FIFO) memory stack. The register 26 is a 16-bit differential register interfacing the buffer 25 with the second processor 20'. The first processor 20 provides the handshake signals required for asynchronous transfers. Each 16-bit word sent to the second processor 20' consists of a combination of operation codes, data, or system status information.

FIG. 9 shows an overall block diagram of the system as applied to a single channel, and further shows coil 11 of the omitted channel. The integrator/amplifiers 15, DAC 27, interface 27', the processors 20 and 20', and interface 20" are shown.

The first processor 20 is suitably mounted on a chassis and includes a suitable input/output board 29 which interfaces with the second processor 20' and also with proximity switches 33 and photodetectors 34 for determining the position of fuel rod 10 during measurement. The input/output board 29 also accepts information from a gamma densitometer 39 which includes gamma detectors 39'. The gamma densitometer 39 is provided to enable the processor 20 to correct for density variations along the travel axis of the fuel rod 10 or material under analysis.

The input/output board 29 further communicates control information to the stepping motors 39" which drive the fuel rods 10 into position and through the sensing coils 11. The input/output board 29 is also connected to a microterminal 49 which is a terminal permitting the control of overall operations. The processor 20 itself includes a Multibus ® microcomputer communications bus (not shown) available from Intel Corporation. Which enables the processor 20 to communicate with devices attached to it directly and indirectly. It receives information from interface 27' and feeds information to DAC 27. The proximity switches 33 indicate the completion of each fuel rod scan. The microterminal 49 is available from Burr-Brown Corporation. It includes a keyboard and a display and enables a human operator to communicate with the processor 20 and to manually control system operation.

Figure 7:
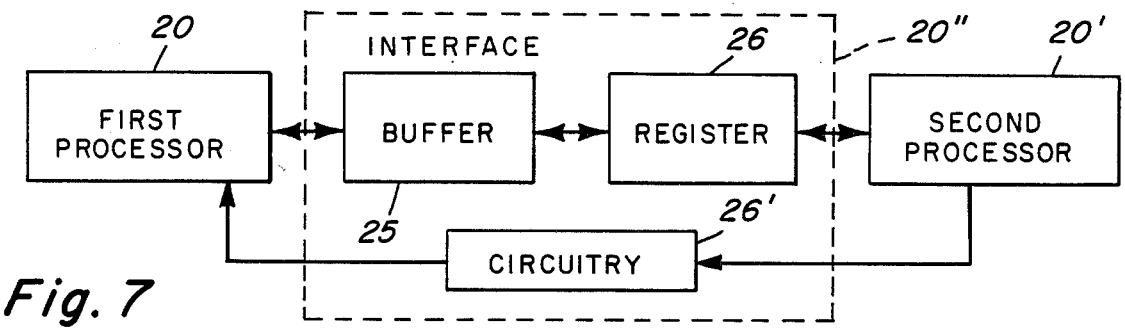
FIG. 7 illustrates the underlying principle of cooperation between the several processors which interact to accomplish the purposes of the instant invention.

The relationship between the two processors 20, 20' employed is best illustrated in FIG. 7. There are particular reasons why two processors 20, 20' are employed. One of the reasons is that the first processor 20 characteristics do not permit the handling of large amounts of data. Additionally, the information handling speed of the first processor 20 is insufficient. Accordingly, the first processor 20 essentially passes the data to the second processor 20' for data handling, and the information needed by the first processor 20 for controlling rod 10 passing through the magnetic pick-up coils 11 is sent back in the form of serial indications through a series-to-parallel converter or circuitry 26'.

In operation, the first processor 20 fills a portion of the data buffer 25. Then, at certain periods indicated by the second processor 20', the data is unloaded to the second processor 20'. This control is performed by a 16-bit differential input register 26 which interfaces the buffer to the second processor 20' and provides the hand-shake signals required for an asynchronous transfer. When the data buffer 25 has data, it sends the data (one 16-bit word at a time) to the register 26. The register 26 then sets a flag which is read by the processor 20'. The flag status indicates that data is available and the processor 20' then reads the data and resets the flag. The process is repeated for the next data word.

The data sent to the second processor 20' arrives at a rate of the order of 50 words per second. The series-to-parallel converter 26' referred to above is a serial communications unit which processes serial data from the second processor 20' and puts it into parallel for transmission to the first processor 20. This occurs at a band rate of approximately 2,400 band. The series-to-parallel converter 26' can be custom made or can be purchased on the free commercial market.

Having the two processors 20, 20' also permits the automatic or semiautomatic operation of the invention. The second processor may be a PDP-11/34 type minicomputer system working in conjunction with dedicated software. In order to operate the system, it must first be initialized. Initialization includes turning on certain power switches on the PDP-11/34 and various other elements of the overall system. It includes calibrating densitometer 39.

FIG. 8A shows a block diagram of interface 27' each including a multiplexer 37(1), a sample and hold unit 37(2), and an analog-to-digital converter unit 37(3). The processor 20 selects the appropriate amplifier 32' or 32" in each channel (i.e., the high or low sensitivity input of each channel) by appropriately addressing the multiplexer 37(1). The sample and hold unit 37(2) performs a function well known to those skilled in the art, as does ADC 37(3).

Figure 8B:
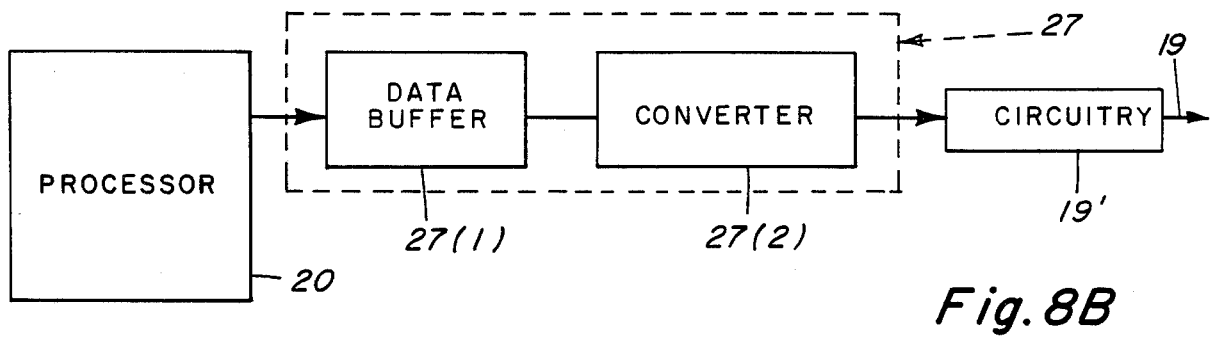
FIG. 8B illustrates the feedback circuit of FIG. 4.

FIG. 8B shows a DAC 27 in block diagram form employable for feedback between the processor 20 and integrator/amplifier 15. In particular, a 12-bit digital to analog converter system is shown including a data buffer element 27(1) and converter unit 27(2).

The multiplexer 37(1) in FIG. 8A, the sample and hold unit 37(2), the ADCs 37(3), the DACs 27(2), and the data buffer 25 are all contained on a single board which is plugged into an Intel Corporation SBC 660 system chassis. The single board is the RTI-1200 Analog Board manufactured by Analog Devices, Inc., Massachusetts. The multiplexer 37(1) can accept up to 32 analog signal sources or channels. However, in this instance, the only inputs dealt with are high and low sensitivity inputs. The sampling is controlled by a processor clock. The analog signal from the integrator/amplifier 15 is digitized by 12-bit ADC 37(3) and is sent to the processor 20 over an 8-bit wide data bus.

The processor 20 is preferably a microprocessor such as an Intel Brand 80/24 Single Board Computer (FIG. 9) and uses software effective for sampling the outputs of each integrator/amplifier 15 or coil network as well as for developing suitable feedback signals for drift correction, which are passed along cables 19 as an input to integrator/amplifier 15. An RTI 1200 board (not shown) provides suitable interfacing.

The enhanced dynamic range of the system is based in part on the positioning of the integrator 18 (FIG. 4) before the amplifier stages 31 and 32, and also on the use of the parallel amplifiers 32' and 32", as explained herein.

The output voltage of each integrator 18 is equal to the integral of the voltage into the integrator, divided by a time constant RC, R being the resistance seen at the input to the integrator times the bypass capacitance C. Accordingly, $V_{out} = -1/RC \int V_{in} dt$. The time constant RC is about 25 milliseconds, which relates to the rate of data acquisition and the scanning rate of the fuel rods 10. This is about one fuel rod per 30 or 40 seconds at a spatial resolution enabling the scanning of fuel element 10 having a roughly one centimeter diameter. Given that time constant, the output drift rate must be less than about 0.5 millivolt per minute, so that during the scan of a single fuel rod, less than about 0.25 millivolt of drift will occur at the output of each integrator/amplifier 15. The output voltage $V_{out}$ may range from $-165$ to $+165$ millivolts, and the input voltage $V_{in}$ may range between 0 to 500 millivolts. A typical input signal variation, however, is in the range of a few millivolts. The full 500 millivolt range is nonetheless required because of ferromagnetic impurities and the presence of the relatively highly ferromagnetic plenum spring 47 (FIG. 2).

The bandwidth of the input voltage $V_{in}$ may range from DC to 10 kilohertz in frequency. That is a characteristic of the output of the coil 11, which in turn relates to the scanning rate of the fuel rod 10.

The accuracy of each integrator 18 must be better than one part in 10,000. The dynamic range required is from plus or minus 0.04 microvolts, to plus or minus 0.5 volts. The linearity of the integrator 18 over the dynamic range must be better than about one part in 20,000 to obtain the required accuracy of weight percent gadolinia in the final output. The gain for a single amplifier stage 31 is in the 5 to 7 range, and both amplifier stages in series have a cumulative gain of about 50 to 70.

The maximum anticipated room temperature drift is about 10 degrees Celsius per minute. Variation within this range is acceptable and does not irreversibly affect the properties of the integrator/amplifier 15. The output drift of each integrator/amplifier 15 is less than 0.5 millivolt per minute.

This ambient temperature drift stability is maintained by mechanical as well as electrical or electronic features of the system. Packaging in a stainless steel thermal buffer unit 100 as shown in FIGS. 5A–5D provides useful thermal inertia and buffering of temperature fluctuations and electromagnetic effects, both ambient and stray, for the circuitry 15. Furthermore, using all-similar metal leads with respect to the circuitry 15 tends to minimize any Seebeck voltages due to the temperature gradients between dissimilar metal contacts. (A Seebeck voltage is that voltage generated by temperature differences between the junctions in a circuit composed of two homogeneous electric conductors of dissimilar composition or, in non-homogeneous conductors, by a temperature gradient in a non-homogeneous region. The magnitude of the voltage depends on the metals and the distribution of temperature in them.)

Figure 5A:
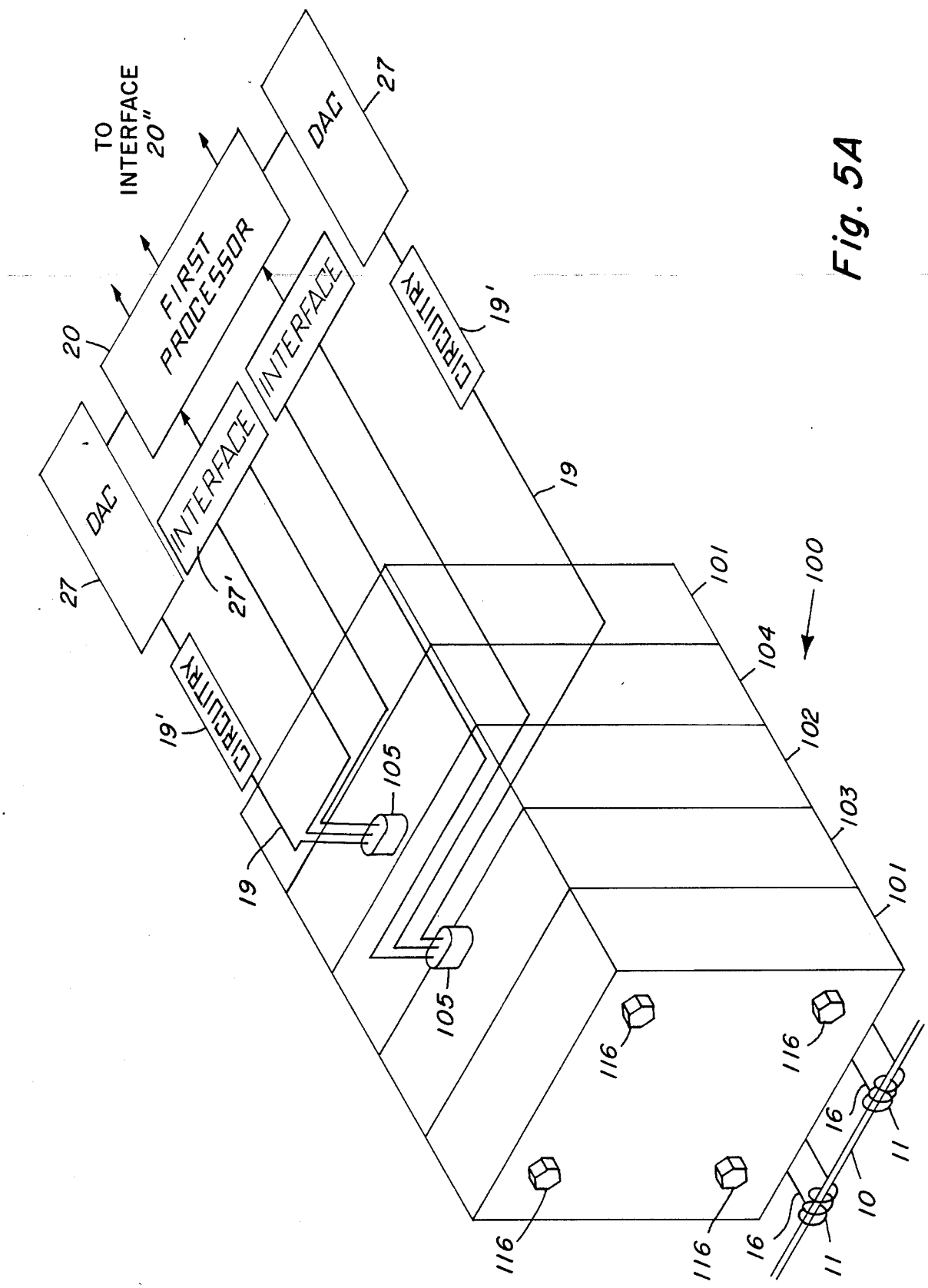

The two channels of integrator/amplifier circuitry 15 are mounted respectively on two three-by-three inch epoxy glass boards, which in turn are mounted inside of a five-by-five inch by one-and-⅝ inch stainless steel unit 100 held together by suitable stainless steel bolts 116, as shown in FIG. 5A. The total unit 100 includes five stainless steel blocks acting as a thermal buffer stainless steel box. The two end blocks 101 and the one center block 102 are solid. The second and fourth blocks, respectively 103 and 104, each have a central void (shown in FIGS. 5B and 5C) for each receiving a single channel of the integrator/amplifier 15. In other words, portions of the second and fourth stainless steel blocks 103 and 104 serve as holding spaces for the integrator/amplifier circuits 15. The spaces carved out of blocks 103, 104 hold the epoxy glass circuit boards which contain the resistors, capacitors, amplifiers and integrators comprising the intergrator/amplifier circuits 15.

FIG. 5A shows leads 16 from each of the integrator/amplifiers 15 to the pick-up coils and also leads 19 to and from the DACs 27 and interfaces 27' and with respect to processor 20. Each of the leads to processor 20 from block 100 are attached to a 9-pin D-series connector 105. One connector 105 is used for each integrator-/amplifier circuit 15. The wire employed for the leads is AWG 30 copper and is Teflon-coated for electrical insulation. The connector pins (not shown) are copper-plated to minimize the Seebeck effect which might establish a potential difference at the bimetallic connection. The wires to the pick-up coils 11 are copper AWG 30, Teflon-coated and are placed in ⅛ inch stainless steel tubing 16' for additional thermal insulation as suggested in FIG. 5B. The construction shown in FIG. 5A reduces signal drift in the integrator/amplifier circuitry 15 to about 0.1 microvolts per degree Celsius. In an environment possibly subject to ambient temperature gradients in the order of ten degrees Celsius per minute, this results in the actual circuitry being subject only to temperature variations on the order of one degree celcius per hour. Similar AWG 30 copper, Teflon-coated wiring is employed to connect the circuitry in block 100 to the pick-up coils 11. In general, all wires including the internal wiring on the circuit board are made of copper material, and the connector pins themselves are plated with copper. Accordingly, there is a consistency in the material used for the electrical connections. By maintaining all of the wires in the system of the same material, the so-called Seebeck effect is greatly reduced or prevented.

FIG. 5B is a side view of either block 103 or 104 of the stainless steel unit 100 which houses the integrator-/amplifier circuits 15 mounted on epoxy glass boards 106. The 9-pin D-type connector 105 is shown mounted on suitable standoffs 107 held on to the stainless steel unit 100 by screws 108 or other suitable means. The wiring between the connector 105 and the integrator-/amplifier circuitry 15 extends through a suitable groove 109 in the body of the second and fourth blocks 103 and 104. Another groove 113 is provided for the leads 16 to the pick-up coils 11. These leads 16 extend through ⅛ inch stainless steel tubing 16'. This is done for shielding purposes. Teflon insulation is provided between the leads 16 and the ⅛ inch stainless steel tubing 16'. FIG. 5C shows a frontal view of the stainless steel unit 100 comprised of the five stainless steel blocks 101–104. Suitable holes 116' for the bolts 116 connecting the blocks 101–104 with one another are shown in phantom. Also indicated are step supports 117 within the blocks 103 and 104 which are used to support the epoxy glass boards 106 holding the integrator/amplifier circuitry 15. This view shows the 9-pin D-type connectors 105 which are used for input to the processor 20 and to feed back a drift correction or compensation signal.

FIG. 5D shows the top of either block 103 or 104, including groove 109 permitting, for example, lead 19 to connect the integrator/amplifier circuitry 15 with circuitry 19'.

The disclosure material herein treats the processing of signals from the integrator/amplifier circuitry 15 according to a specific method. In particular, this relates to the development of difference signals based upon the subtraction of the output of one channel 15 from the other. The result obtained involves the signature analsis of the fuel element 10 profile. The basic measurement concept implemented by the circuitry shown in FIG. 6 draws its background from the Grossman et al. '939 patent, referred to above. Nonetheless, the coil circuitry of FIG. 2 may be employed according to a technique somewhat similar to the '939 patent.

In particular, the output signals from amplifiers 32' (FIG. 4) can be treated as voltage signals $V_1$ and $V_2$. For simplicity, the selected output signal from the selected coil channel or circuit 15 will be called $V_1$ and that of the other coil circuit, $V_2$. The non-selected signal (e.g., stemming from amplifier 32'') is referred to in the small case "$v_1$" and "$v_2$" as the case may be. $V_1$ and $V_2$ (or $v_1$ and $v_2$, small case) are integrated voltage signals proportional to the field magnitude H, times the susceptibility change dX, and the number of turns of coil N, i.e., $V_{1,2} = NHdX$. According to this relationship, known mathematical methods, and the information contained in the Grossman et al '939 patent, the distribution and content of the desired additive or absorber in fuel rod 10 comprising zones of differing additive concentration can be determined.

It follows that the selected composite output signal, taking into account corresponding lumped gain constants $K_1$ and $k_2$, can be expressed in terms of $K_1V_1$ and $K_2V_2$. Defining a difference signal $D = K_1V_1 - K_2V_2$ permits the factoring out of the high magnitude signal contribution of the ferromagnetic portions of the fuel element 10. Accordingly, the difference signal is based upon measurements under significantly different magnetic field strengths, both nonetheless under conditions of ferromagnetic saturation. A solution of $V_1$ and $V_2$ can thus be obtained for known values of $K_1$ and $K_2$, which are established as constants by suitably setting the amplifier gains in FIG. 4.

Figure 6:
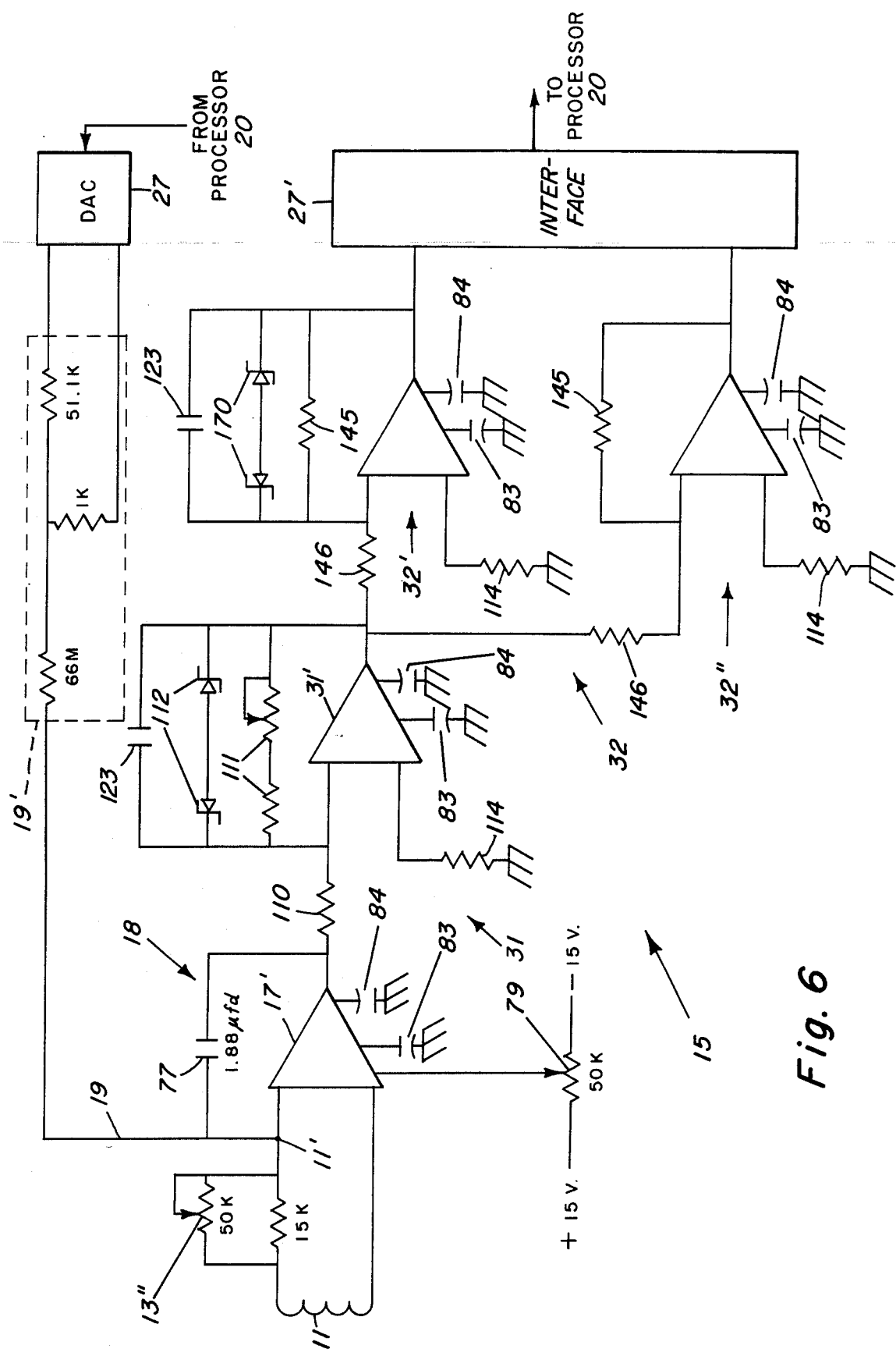
FIG. 6 shows details of the circuit design of a single channel of the scheme shown in FIG. 4.

Turning now to the details of the circuitry shown in FIG. 6, there is shown in stages an integrator/amplifier 15. Two such integrator/amplifiers 15 have already been shown in FIG. 4, each connected to a corresponding detection or pick-up coil 11. One is disposed for operation in a high direct current magnetic field and the other is disposed in a relatively lower but still sufficiently high DC magnetic field to insure ferromagnetic saturation.

In FIG. 6 as in FIG. 4, an integrator 18 is shown preceding amplifiers 31, 32', and 32''. The integrator 18 is suitably electrically connected to the coil 11 at terminal 11'. This terminal 11' also serves as a signal input for feedback from processor 20 as will be shown.

Since there are two integrator/amplifiers 15 of the kind shown in FIG. 6, serving as separate channels in FIG. 4, it is necessary to adjust the two channels for compatible operation. Accordingly, certain adjustable resistive members 13'' precede terminal 11' at the input of the integrator/amplifier 15. This permits balancing the separate circuits 15 with respect to one another.

The integrator 18 includes an operational amplifier 17', such as for example a 234L type device, with capacitors 77 in the feedback loop. For practical operation, these capacitors 77 are as close to ideal capacitors as possible, insofar as minimizing leakage currents is concerned. These capacitors 77 accordingly provide a very direct high current resistance. Films on the surface of the capacitors 77 should not provide any leakage path to current, and the capacitors must be truly linear. Multiple capacitors 77 are provided in this embodiment to reach the desired total capacitance value while maintaining low leakage and low surface conduction characteristics. For example, 0.47 microfarad capacitors are suitable for application to the instant invention. In parallel, four such capacitors 77 result in a lumped capacitance value of about 1.88 microfarads, which provides an appropriate time constant and gain function for the instant embodiment.

Each integrator/amplifier 15 includes an offset adjustment permitting compensation for manufacturing tolerances that exist in such commercial products. The offset adjustment is provided by a variable resistor 79 subject to a voltage range from −15 to +15 volts. The value of the total resistance is 50K ohm. Capacitors 83 and 84 are both 0.1 microfarads. These serve a bandpass function to eliminate the introduction of high-frequency noise.

The amplification factor of integrator 18 is approximately 500. To minimize drift problems related to temperature, the resistors and amplifiers selected have a negative temperature coefficient of resistivity of about 0.01 percent per degree Celsius. The capacitors have an insulation resistance greater than 7.5 megohms. There is a requirement for limiting capacitance drift to the order of plus or minus 0.03 percent under a maximum temperature coefficient range of plus or minus one hundred parts per million per degree Celcius. In order to resolve any drift problems that may be related to noise, the amplifier 17' selected must be of an ultra-low noise type (i.e., it must contribute a noise signal on the order of 0.5 microvolts peak-to-peak or less). Overall, the amplifiers 17' selected have an extremely low drift which is in the order of 0.1 microvolts per degree Celsius and they have a long-term stability on the order of five microvolts per year.

Connected to the output of the integrator 18 is a first amplifier stage 31 effective for amplifying the integrated signal from the integrator 18. An Analog Devices 741-type operational amplifier 31' is effective for this particular amplifier circuit 31. The non-inverting input of the amplifier 31' provides a ground reference through a 5.11K ohm resistor 114. The input side of amplifier 31' connects with the output of integrator 18 through a 5.11K resistor 110. Resistor 110 defines the circuit gain in conjunction with additional resistors 111 having a resistance of up to 35.5K ohms, and including a variable gain adjustment resistor of up to 10K ohm. For example, if the variable gain resistor is set at 10K ohm, the gain of amplifier stage 31 is found by calculating the ratio of the sum of resistors 111 to input resistor 110 at 5.11K ohm, resulting in a gain of approximately seven.

Suitably-valued zener diodes 112 are provided in the feedback loop for amplifier circuitry 31 to limit possibly excessive voltage excursions at the output of amplifier 31'. When the voltage exceeds the zener voltage of one of the diodes 112, a low impedance path is provided around amplifier 31', effectively reducing gain and preventing amplifier saturation. Zener diodes 112 are back-to-back, keeping both positive and negative voltage excursions between defined bounds. In each case and as appropriate for a given voltage excursion, one of zener diodes 112 will conduct as an ordinary diode and the other as a zener diode in breakdown or avalanche.

A 0.01 microfarad capacitor 123 is provided across resistors 111 and diodes 112 to perform a filter function and to limit the high frequency response of amplifier 31'. This minimizes high frequency noise in the output signal of integrator/amplifier 15.

The analysis of amplifier circuit 31 immediately above essentially applies to the amplifier circuits 32' and 32" as well. Again, the gain of the respective amplifier circuits is found by determining the ratio of the feedback resistor(s) 145 to the input resistor 146, which for the two circuits 32' and 32" respectively results in a gain of ten and one. The cumulative gain of amplifier stage 31 in series with amplifier stage 32 is accordingly seventy or seven, depending on the output branch being considered. The various capacitance elements 83 and 84 shown in both circuits 31 and 32 serve the same bypass or noise-reduction purposes as before. The zener diodes 170 of circuit 32' act in the same basic fashion as those of circuit 31. The output of circuit 32" requires no zener diode protection because with a gain of one, no saturation can occur, in view of the zener protection provided for circuit 31.

The feedback or attenuator circuitry 19' returns a drift correction signal from the processor 20 through DAC 27. The attenuator network 19' limits the amplitude of the correction signal applied to the input side of integrator 18. In this embodiment, the nature of signal is to provide an input to the integrator/amplifier 15 over a period of thirty seconds. During this period of time, no signal variation occurs due to any changes in coil 11, since the drift correction is based upon measurements made in air. Any change in voltage noted by the processor 20 is reflected in a compensatory change on the input side of the integrator/amplifier 15. The magnitude of the correction signals is relatively small—on the order of picoamperes, and tens of nanovolts. This maintains a quiescent output voltage from amplifiers 32' or 32" of about five volts.

The person skilled in the art will realize several striking advantages in the method of this invention. In particular, he will realize that it is possible to practice qualitative control and quantitative control on nuclear fuel materials, be they in powder or pellet form, or assembled into fuel elements. Such quality control can be practiced non-destructively; that is, if the nuclear fuel material passes the test, it can be utilized in nuclear reactors. Further the equipment involved in the practice of this method is inexpensive; it is commonly available, requires low maintenance, and is relatively easy to operate. Additionally, the practice of the method of this invention gives rapid results, enabling the invention to be conveniently automated and incorporated in fuel assembly lines in the manufacture of nuclear fuel materials.

This invention can be utilized with various forms of nuclear fuel materials which contain at least one fissionable isotope. A person skilled in the art will realize that nuclear fuel in elemental or compound forms, such as oxides, carbides, borides, nitrides and mixtures thereof as well as other ceramic compounds of fissionable isotopes, are comprehended in the practice of this invention. In one particular preferred practice of this invention, the nuclear fuel material is in the form of an oxide composition of uranium since this type of composition is particularly popular for the generation of electrical power by nuclear fission chain reactions.

The foregoing description is susceptible of reasonable modifications that may occur to those skilled in the art. However, this invention is not meant to be limited to the embodiment just shown and described. The claims set forth the inventive concept and are intended to cover all modifications coming within the spirit and scope of the invention described herein.

What is claimed is:

1. A system for analyzing the additive, paramagnetic material content of a nuclear fuel rod, said rod further including a base paramagnetic material and ferromagnetic impurities, the susceptibility of said additive material being measurably larger than that of said base material;

said system comprising:

means for establishing a pair of direct current magnetic fields of different strengths;

first and second inductive coils each positioned in one of said magnetic fields;

means for moving said nuclear fuel rods through said inductive coils to provide an electrical output indication from each coil representative of susceptibility changes caused by the movement of said fuel rod through said coil;

first and second signal channels coupled to said first and second coils respectively, each of said channels including an integrating means at the channel input followed by a plurality of serially connected amplifier stages, each of said channels being responsive to said output indication of the corresponding coil to provide a channel output signal including a quiescent signal portion when said fuel rod is absent from both of said coils;

means for establishing a reference value corresponding to each of said quiescent signals;

means corresponding to each of said channels for correcting signal drift in said channel, said drift correction means including means for repeatedly sampling said quiescent signal, means for averaging said sampled signals, means for comparing said averaged quiescent signal with the corresponding reference value, means responsive to said comparing means for deriving a drift correction signal, and feedback means for applying said drift correction signal to said channel input; and means for analyzing the output signals derived from respective ones of said channels when said fuel rod passes through said coils to determine said additive paramagnetic material content.

2. The system of claim 1 wherein each of said channels further includes a multiplexer, the last one of said amplifier stages in each channel including a plurality of amplifiers of different gains connected in parallel between the output of the previous amplifier stage and said multiplexer; and means including said multiplexer for selecting from among said plurality of amplifiers in each channel the amplifier which has the highest gain and whose output signal is below a predetermined threshold value and for applying said last-recited output signal to said drift correction means.

3. The system of claim 1 and further including a metal buffer unit surrounding said first and second channels adapted to insulate said channels from ambient temperature fluctuations.

4. The system of claim 1 wherein in each of said channels all electrical connections consist of the same metal.

5. The system of claim 1 wherein at least some of the amplifiers in the respective stages of each channel are individually connected in parallel with a zener diode circuit, each of said zener diode circuits including a pair of series-connected, oppositely poled zener diodes adapted to limit excessive voltage excursions in the output of the connected amplifier.

6. The system of claim 1 wherein at least some of the amplifiers in the respective amplifier stages of each channel are individually connected in parallel with a capacitor, each of said capacitors being adapted to filter out high frequency noise from the output of the connected amplifier.

7. The system of claim 1 and further comprising a digital processor which includes said averaging means, said comparing means and said means for deriving a drift correction signal;

each of said channels further including an analog-to-digital converter for providing the corresponding channel output signal in digitized form to said digital processor; and said feedback means for each channel including a digital-to-analog converter connected to the output of said digital processor, and an attenuator for modifying said drift correction signal in analog form.

8. A method of correcting for drift in a system for analyzing the additive paramagnetic material content of a nuclear fuel rod, said system including first and second inductive coils each positioned in a separate, direct current magnetic field, means for moving said nuclear fuel rod through said inductive coils, and first and second signal channels each having its input coupled to one of said coils and adapted to provide an output signal in response to the output indication provided by said coil, each of said output signals including a quiescent signal portion when said fuel rod is absent from both of said coils;

said method comprising for each of said channels, the steps of:

establishing a reference value;

repeatedly sampling said quiescent signal;

averaging said sampled signals;

comparing said averaged quiescent signal with said reference value to determine an error value;

deriving a drift correction signal from said error value; and applying said drift correction signal to said input of said channel.

9. The method of claim 8 wherein each of said channels further includes integrating means at its input followed by a plurality of serially connected amplifier stages, and a multiplexer, the last one of said amplifier stages including a plurality of amplifiers of different gains connected in parallel between the output of the previous amplifier stage and said multiplexer;

said method further including the step, for each channel, of selecting from among said plurality of amplifiers of said last amplifier stage the output signal of the highest gain non-saturated amplifier.

* * * * *